United States Patent [19]

Oppenländer et al.

[11] Patent Number: 5,756,078

[45] Date of Patent: May 26, 1998

[54] AQUEOUS PREPARATIONS, COMPRISING ALKYL POLYGLYOSIDES AND A POLYMER

[75] Inventors: Knut Oppenländer, Ludwigshafen; Günter Oetter, Frankenthal; Hans-Ulrich Wekel, Ellerstadt, all of Germany

[73] Assignee: BASF Aktiengesellschaft, Ludwighafen, Germany

[21] Appl. No.: 794,569

[22] Filed: Feb. 3, 1997

[30] Foreign Application Priority Data

Feb. 8, 1996 [DE] Germany ............... 196 04 466.9

[51] Int. Cl.$^6$ .................................................. A61K 7/06
[52] U.S. Cl. ............................................... 424/70.13
[58] Field of Search ....................................... 424/70.13

[56] References Cited

U.S. PATENT DOCUMENTS

| 5,166,302 | 11/1992 | Werner et al. | |
|---|---|---|---|
| 5,409,628 | 4/1995 | Heinz et al. | 424/70.13 |
| 5,464,874 | 11/1995 | Balzer | 424/70.13 |
| 5,478,562 | 12/1995 | Cauwet et al. | 424/401 |
| 5,514,369 | 5/1996 | Salka et al. | 424/70.13 |

FOREIGN PATENT DOCUMENTS

| 353 735 | 2/1990 | European Pat. Off. . |
|---|---|---|
| 1 358 430 | 7/1974 | United Kingdom . |

OTHER PUBLICATIONS

Collids and Surfaces, Hulden, Physicochemical and Eng. Asp. 82 (1994) 263–277.

*Primary Examiner*—Joseph L. Schofer
*Assistant Examiner*—N. Sarofim
*Attorney, Agent, or Firm*—Keil & Weinkauf

[57] ABSTRACT

Aqueous preparations comprising an alkyl polyglycoside and a polyethylene glycol ether derivative of the formula I

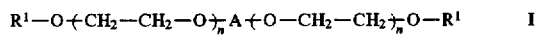

where $R^1$ is alkyl having 8–22 carbon atoms,
A is a divalent radical derived from a diisocyanate and
n is 20–400 are described.

10 Claims, No Drawings

AQUEOUS PREPARATIONS, COMPRISING ALKYL POLYGLYOSIDES AND A POLYMER

The present invention relates to aqueous preparations which comprise alkyl polyglycosides and polyethylene glycol ether derivatives.

The compositions according to the invention are, in particular, cosmetic compositions.

Cosmetic compositions which contain alkyl polyglycosides and polymers are known from the prior art (SÖFW Journal, 121st year, 8/95, pages 598–611). It is mentioned that polymers such as, for example, xanthan gum and alginates are used in alkyl polyglycoside formulations as viscosity-regulating additives (see p. 607, 1st column).

EP 511 566 A1 discloses aqueous surfactant preparations having increased viscosity which, beside base surfactants, contain alkyl polyglycosides and a polymer, derivatives of alkoxylated polyhydric alcohols being mentioned as polymers.

EP 408 965 and EP 388 810 disclose detergent compositions which contain alkyl glycosides.

DE 42 17 673 A1 discloses electrolyte-thickenable surfactant combinations which contain alkyl polyglycosides, carboxymethylated alkanol ethoxylate and monoalkyl sulfosuccinate in very specific quantitative ratios.

Hydrophobically modified urethane ethoxylate thickeners of the formula alkyl—NHC-(E$_n$—DI)$_2$—E$_n$—OCONH-alkyl where E=ethylene oxide and DI=diisocyanate are known for use in paints from Colloids and Surfaces A: Physicochemical and Engineering Aspects, 82 (1994) 263–277.

DE 22 04 841 and DE 20 54 885 describe pigment printing pastes which contain polyethylene glycol ether derivatives as thickeners.

It is an object of the present invention to make available aqueous preparations which contain alkyl polyglycosides, ie. a constituent based on renewable raw materials which is advantageous from toxicological, ecological and physiological points of view. At the same time, the preparation should have a high viscosity without relatively large concentrations of electrolytes (such as, for example, NaCl) being necessary.

We have found that this object is achieved by aqueous preparations which, beside alkyl polyglycosides, contain polyethylene glycol ether derivatives of the formula I

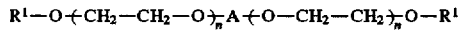

where

R$^1$ is alkyl having 8–22 carbon atoms,

A is a divalent radical derived from a diisocyanate and n is 20–400.

These preparations are preferably cosmetic compositions, in particular hair treatment compositions, shower baths, shower gels, but also facial cleansers, handwashing pastes and lotions. Hair treatment compositions which may be mentioned are: shampoos, hair rinses, styling gels and waving compositions.

The aqueous preparations according to the invention preferably contain an additional surfactant. This surfactant can be surfactants customary in aqueous, in particular cosmetic preparations, such as, for example, fatty alcohol ether sulfates, fatty alcohol sulfates, carboxymethylated fatty alcohol ethoxylates, fatty alcohol ether sulfosuccinates, alkanesulfonates, fatty acid salts, alkylbetaines, ampholytes, fatty alcohol ethoxylates, fatty acid sorbitan esters, ethoxylated sorbitan esters, sugar esters and their mixtures count as base surfactants, the chain length of the saturated or unsaturated, straight-chain or branched alkyl chain in each case being 8 to 22, preferably 10 to 20 carbon atoms, and the cations of the anionic surfactants being Na, K, NH$_4$, C$_2$-C$_3$-alkanolammonium or Mg. The degrees of ethoxylation in the case of the fatty alcohol ether sulfates are from 1 to 5 (preferably from 2 to 4), in the case of the carboxylated ethoxylates from 2 to 15 (3 to 10), in the case of the fatty alcohol ether sulfosuccinates from 1 to 6 (2 to 4) and in the case of the fatty alcohol ethoxylates from 2 to 25 (2 to 15) mol of ethylene oxide/mole.

The alkyl polyglycosides contained in the preparations according to the invention preferably corresond to the formula II

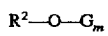

where

R$^2$ is a linear or branched alkyl radical having 8 to 18, preferably 10–16 C atoms, G is a polyglycosyl radical and m is 1.1–5, preferably 1.1–2.5.

In the above formula I, R$^1$ is preferably an alkyl radical having 10–20 C atoms, A is preferably the divalent radical derived from an aromatic diisocyanate and n is preferably 60–300.

The preparations according to the invention preferably contain 1–20% by weight of alkyl polyglycoside and 0.05–1, in particular 0.1–0.5, % by weight of polyethylene glycol ether derivatives of the formula I.

If, beside the alkyl polyglycosides and the customary base surfactants, the polyethylene glycol derivatives of the formula I according to the invention are employed, then even with additions of from 0.2 to 0.8% by weight a thickening of 4000–18,000 mPa.s is achieved.

The preparation of the polyethylene glycol ether derivatives is given in detail in DE 22 04 841, which is expressly referred to.

The alkyl polyglycosides employed according to the invention are commercially available, which is pointed out in the SÖFW Journal, 121st year, 8/95, page 598. They can be prepared in a known manner on the basis of renewable raw materials, see, for example, EP 511 466 A1, column 3. It is indicated there that, for example, dextrose can be reacted with n-butanol in the presence of an acidic catalyst to give butyl polyglycoside mixtures which can likewise be transglycosidated with long-chain alcohols, likewise in the presence of an acidic catalyst, to give the desired alkyl polyglycoside mixtures.

The structure of the products can be varied within certain limits. The alkyl radical R$^2$ is fixed by the choice of the long-chain alcohol. The surfactant alcohols having 10 to 18 C atoms accessible on the large industrial scale, in particular native fatty alcohols from the hydrogenation of fatty acids or fatty acid derivatives, are convenient for economic reasons. Ziegler alcohol or oxo alcohols can also be used.

The polyglycosyl radical G$_m$ is fixed on the one hand by the choice of the carbohydrate and on the other hand by the setting of the mean degree of polymerization n, eg. according to DE-OS 19 43 689. In principle, as is known, polysaccharides, eg. starch, maltodextrins, dextrose, galactose, mannose, xylose etc. can be employed. The carbohydrates of starchy maltodextrins and particularly dextrose available on the large industrial scale are preferred. As the alkyl polyglycoside syntheses, which are of economic interest, do not proceed regio- and stereoselectively, the alkyl polyglycosides are always mixtures of oligomers which in turn are mixtures of various isomeric forms. They are present together with α- and β-glycosidic bonds in pyranose and furanose form. The sites of linkage between two saccharide residues are also different.

Alkyl polyglycosides employed according to the invention can also be prepared by mixing alkyl polyglycosides with alkyl monoglycosides. The latter can be recovered or concentrated from alkyl polyglycosides, for example, according to EP-A 0 092 355 by means of polar solvents, such as acetone.

The degree of glycosidation is expediently determined by means of $^1$H-NMR.

In comparison with the surfactants employed in cosmetic cleansing compositions, the alkyl polyglycosides count as extremely environmentally tolerable. Thus the degree of biodegradability for the alkyl polyglycosides according to the invention determined by means of purification plants simulation model/DOC analysis is 96±3%. This figure is to be seen from the background that in this test method (total degradation) a degree of degradation of >70% means that the substance counts as readily degradable.

Even the acute oral toxicity LD 50 (rats) and the aquatic toxicity LC 50 (golden orfe) and EC 50 (daphnia) values of >10,000 mg/kg, 12 and 30 mg/l are more favorable by a factor of 3 to 5 than the corresponding values for the most important surfactants today. The same applies to the skin and mucous membrane tolerability, which is particularly important in cosmetic formulations.

Salts such as, for example, alkali metal, ammonium and/or alkaline earth metal halides, sulfates or phosphates can additionally be added in small amounts to the preparations according to the invention.

The preparations according to the invention surprisingly also have a good viscosity when no anionic surfactants are added.

In a known manner, the aqueous preparations according to the invention can contain further components which are important for the particular intended use. Those suitable are silicone surfactants, protein hydrolyzates, fragrances, opacifying and pearl luster agents, refatting agents, silicone oils, moisturizing agents, preservatives, skin cosmetic active ingredients, plant extracts, buffer substances, complexing agents, etc.

EXAMPLES

Example 1

Thickening of a shampoo base with sodium lauryl ether sulfate (containing about 2 mol of EO, about 28% active substance in H$_2$O) (Texapon® N 28) and lauryl polyglucose (based on C$_{12}$–C$_{16}$-fatty alcohol, having a value for m of 1.4–1.45) (Plantaren® 1200)

Recipe (% by weight):

22.0 Texapon® N 28
16.0 Plantaren® 1200
0.62 citric acid 10%
0.5 thickener of the formula III
water to 100.0

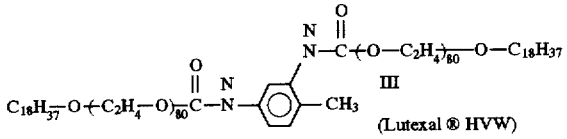
(Lutexal ® HVW)

| Appearance; | pH; | Viscosity (Haake VT 02, spindle 2) |
|---|---|---|
| clear, highly viscous; | pH: 6.06; | 1500 mPa · s |

Example 2

Thickening of a shampoo base without Texapon® N 28
Recipe (% by weight):
30.0 Setacin 103 special (disodium laureth sulfosuccinate)
18.0 Plantaren 1200
3.0 amphotenside B 4 (Cocoamidopropyl betain) thickener as indicated below
Water to 100.0

| Thickener | Appearance; | pH; | Viscosity (Haake VT 02; spindle 1) |
|---|---|---|---|
| +2% Lutexal HVW | clear, highly viscous | pH: 5.52 | 7000 mPa · s |
| +2.0% NaCl | clear, liquid; | pH: 5.38 | 400 mPa · s (too thin) |

Example 3

Shampoo base thickened with Lutexal HVW—concentration series
Recipe (% by weight):
22.0 Texapon® N 28
16.0 Plantaren® 1200
0.62 citric acid 10% thickener as indicated below
Water to 100.0

| | Appearance; pH; Viscosity (Haake VT 02; spindle 1) | | |
|---|---|---|---|
| Thickener | after preparation: | after 24 h RT; | after 4 days RT |
| +0.35% Lutexal HVW | clear, pH: 6.01, 1400 mPa · s | clear 1700 mPa · s | clear, 1800 mPa · s |
| +0.40% Lutexal HVW | clear, pH: 6.01, 2100 mpa · s | clear, 2900 mPa · s | clear, 2800 mPa · s |
| +0.50% Lutexal HVW | clear, pH: 5.94, 4200 mPa · s | clear, 5000 mPa · s | clear, 5000 mPa · s |
| +0.60% Lutexal HVW | clear, pH: 5.97, 8500 mPa · s | clear, 9500 mPa · s | clear, 9500 mPa · s |

We claim:
1. An aqueous preparation, comprising an alkyl polyglycoside and a polyethylene glycol ether of the formula I

$$R^1-O+CH_2-CH_2-O\}_n-A+O-CH_2-CH_2\}_n-O-R^1 \quad I$$

where $R^1$ is alkyl having 8–22 carbon atoms

A is a divalent radical derived from a diisocyanate and n is 20–400.

2. A preparation as defined in claim 1, wherein the preparations are cosmetic compositions.

3. A preparation as defined in claim 2, wherein the cosmetic compositions are hair treatment compositions, shower baths or shower gels.

4. A preparation as defined in claim 1, which additionally comprises a surfactant.

5. A preparation as defined in claim 1, which additionally comprises alkyl polyglycosides of the formula II $$R^2\text{—O—}G_m \qquad \text{II}$$

where $R^2$ is a linear or branched alkyl radical having 8 to 18 C atoms or mixtures thereof, G is a polyglycosyl radical and m is 1.1–5.

6. A preparation as defined in claim 1, wherein, in formula I $R^1$ is alkyl having 10–20 C atoms, A is a divalent radical derived from an aromatic diisocyanate and n is 60–300.

7. A preparation as defined in claim 5, wherein, in formula II $R^2$ is a linear alkyl radical having 10–16 C atoms and n is 1.1 to 2.5.

8. A preparation as defined in claim 1, which comprises 1 to 20% by weight of alkyl polyglycoside and 0.05 to 1% by weight of polyethylene glycol ether of the formula I.

9. A preparation as defined in claim 1, wherein, in formula I $R^1$ is a $C_{18}H_{37}$ radical, A is a radical (A.1)

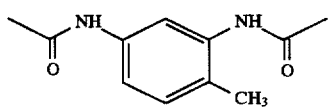 (A.1)

and n is 80.

10. A preparation as defined in claim 1, wherein, in formula I A is a divalent radical derived from an aromatic diisocyanate.

* * * * *